United States Patent
Buhr et al.

(10) Patent No.: US 6,605,217 B2
(45) Date of Patent: Aug. 12, 2003

(54) APPARATUS FOR HIGH PRESSURE FLUID FILTRATION

(75) Inventors: Mark S. Buhr, Huntington Beach, CA (US); Adib G. Daoud, San Diego, CA (US); Derek J. Daw, Costa Mesa, CA (US); John E. Merritt, San Clemente, CA (US)

(73) Assignee: TherOx, Inc., Irvine, CA (US)

( * ) Notice: Subject to any disclaimer, the term of this patent is extended or adjusted under 35 U.S.C. 154(b) by 0 days.

(21) Appl. No.: 10/074,156

(22) Filed: Feb. 12, 2002

(65) Prior Publication Data

US 2002/0070182 A1 Jun. 13, 2002

Related U.S. Application Data

(62) Division of application No. 09/312,181, filed on May 14, 1999, now Pat. No. 6,346,192.

(51) Int. Cl.[7] .............................................. B01D 29/58
(52) U.S. Cl. ..................... 210/335; 210/339; 210/446; 210/450; 210/489; 210/500.25; 210/510.1
(58) Field of Search ................................ 210/767, 227, 210/314, 323.1, 335, 339, 445, 446, 450, 451, 453, 455, 500.25, 510.1, 488–491

(56) References Cited

U.S. PATENT DOCUMENTS

| | | | |
|---|---|---|---|
| 604,931 A | * 5/1898 | Eisendrath | 210/445 |
| 3,133,132 A | * 5/1964 | Loeb et al. | 264/49 |
| 3,295,684 A | * 1/1967 | Webb | 210/314 |
| 3,300,051 A | * 1/1967 | Mitchell | 210/339 |
| 3,567,632 A | * 3/1971 | Richter et al. | 210/321.6 |
| 3,661,724 A | * 5/1972 | Strickler | 205/788 |
| 3,966,439 A | * 6/1976 | Vennos | 73/863.22 |
| 4,055,498 A | * 10/1977 | Radnoti | 210/94 |
| 4,313,828 A | * 2/1982 | Brownlee | 210/198.2 |
| 4,362,621 A | * 12/1982 | Dobna et al. | 210/450 |
| 4,713,344 A | * 12/1987 | Markhart, III | 435/281 |
| 5,221,483 A | * 6/1993 | Glenn et al. | 210/641 |
| 5,342,517 A | * 8/1994 | Kopf | 210/228 |
| 5,376,240 A | * 12/1994 | Kaczur et al. | 205/617 |
| 5,527,466 A | * 6/1996 | Li et al. | 210/636 |
| 5,573,668 A | 11/1996 | Grosh et al. | |
| 5,589,062 A | * 12/1996 | Rice | 210/198.2 |
| 5,647,976 A | * 7/1997 | Rothe et al. | 210/137 |
| 5,798,041 A | * 8/1998 | Zuk, Jr. | 210/456 |
| 5,849,249 A | * 12/1998 | Jones et al. | 422/101 |
| 6,346,192 B2 | 2/2002 | Buhr et al. | |

* cited by examiner

Primary Examiner—W. L. Walker
Assistant Examiner—David Sorkin
(74) Attorney, Agent, or Firm—Margaret A. Kivinski

(57) ABSTRACT

A bacterial fluid filter includes a filter element supported by a backing member. The filter element and backing member are sealed, e.g., with one or more o-ring seals, in a housing to provide a filter assembly capable of filtering fluid under relatively high pressure. In one embodiment, a filter element, backing member, and seal are disposed in a removable and disposable housing that is sized to fit within a filter housing.

12 Claims, 2 Drawing Sheets

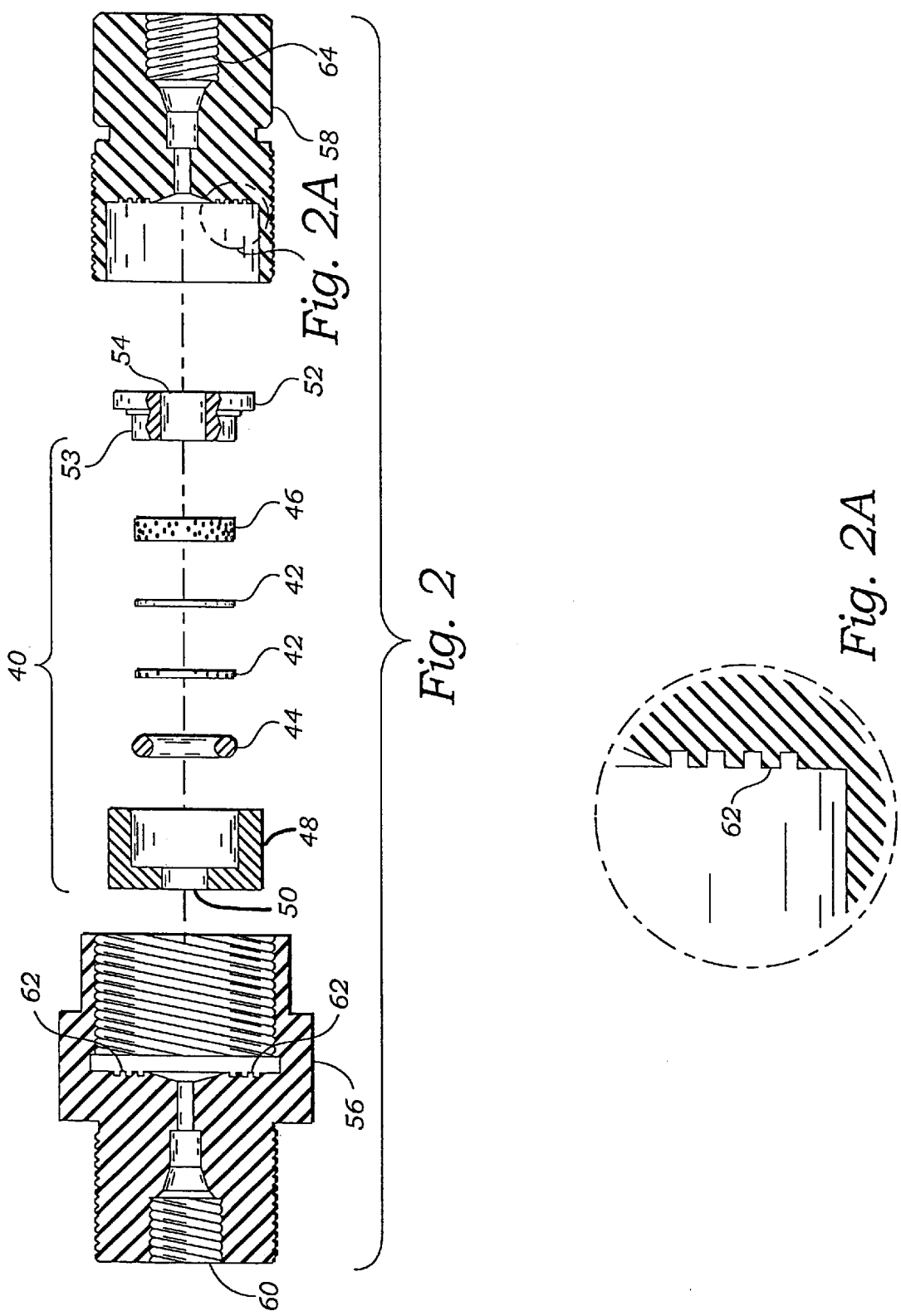

APPARATUS FOR HIGH PRESSURE FLUID FILTRATION

CROSS-REFERENCE TO THE RELATED APPLICATIONS

This application is a divisional of U.S. patent application Ser. No. 09/312,181, filed May 14, 1999, now U.S. Pat. No. 6,346,192 which is incorporated herein by reference.

FIELD OF THE INVENTION

The present invention relates generally to an apparatus for filtering a high pressure fluid stream and, more particularly, to a filter assembly for removing bacteria and other foreign materials from high pressure physiologic fluid streams.

BACKGROUND OF THE INVENTION

In many applications it is desirable to remove bacteria and other foreign materials from fluids prior to delivery of the fluids to a particular desired location. For example, in the medical field, fluids routinely are filtered for sterilization in conjunction with their delivery to catheters for infusion into a patient. Typically, such filtering is accomplished by the placement of a filter media comprising a porous membrane in the fluid flow path.

There are many different types of commercially available filter media, e.g., nylon, polyethersulfone, teflon, polycarbonate, polyester, polytetrafluoroethylene, polypropylene, cellulose, glass fiber, stainless steel, monel, inconel, silver and gold. A filter membrane generally may be described by its "mean path," i.e., the average size of the pores in the filter media, and/or its "absolute path," i.e., the size of the largest pores in the filter media A filter membrane's absolute path corresponds to the size of the smallest particle that can be filtered out of a fluid flow path by the filter membrane. For medical applications in which absolute sterilization is required, a filter membrane having an absolute path of not greater than about 0.2 micron typically is required.

Filter membranes come in a variety of shapes and sizes. Filter membranes may be mounted in line or in panel, and they are typically disposed within a filter holder, either alone or in combination with additional pre-filters, screens, etc. For examples of commercially available filter devices, see, e.g., the 1995 Microfiltration & Laboratory Products Catalog, Poretics Corporation, Livermore, Calif.

Many fluids to be infused into patients are not delivered from a high pressure source, e.g., pressures up to about 5500 p.s.i. or higher. For that reason, conventional fluid filtering devices such as those referred to above typically are not designed to withstand high pressure environments. Under high pressure conditions, the porous membranes of conventional filter devices may burst, allowing bacteria and other unwanted materials to pass. Accordingly, there remains a need for a filter assembly capable of removing bacteria and other foreign materials from high pressure fluid streams.

The present invention may address one or more of the problems set forth above.

SUMMARY OF THE INVENTION

Certain aspects commensurate in scope with the disclosed embodiments are set forth below. It should be understood that these aspects are presented merely to provide the reader with a brief summary of certain forms the invention might take and that these aspects are not intended to limit the scope of the invention. Indeed, the invention may encompass a variety of aspects that may not be set forth below.

The copending U.S. patent application entitled "Filtration of Gas-Containing Fluids" filed on Apr. 30, 1999, by James Richard Spears, Ser. No. 09/302,978, now abandoned, is herein incorporated by reference herein for all purposes.

In one embodiment of the present invention, an apparatus for filtering a high pressure fluid stream is provided. Advantageously, the high pressure fluid stream comprises a flow of a fluid in which a gas (e.g., oxygen, nitrogen, carbon dioxide, air) is dissolved. Advantageously, the dissolved gas volume normalized to standard temperature and pressure is between about 0.5 and about 3 times the volume of the solvent. The fluid passing through the filtering apparatus advantageously comprises a fluid to be provided at a given site in a gas-supersaturated state. Examples (without limitation as to the scope of the present invention) include fluids that are to be delivered into blood, infused into a patient, brought into contact with tissues, etc., such as oxygen-supersaturated fluids.

The apparatus comprises a filter assembly stack disposed within a filter housing assembly. The filter assembly stack comprises a first o-ring, a filter membrane, a membrane backing member, and a second o-ring. The filter housing comprises a bulkhead and a cap.

The filter assembly stack and the housing assembly advantageously are adapted and assembled so that when the cap and bulkhead are joined, e.g., by threaded engagement, with an adhesive, etc., the o-rings are compressed, so as to create a sealed continuous fluid flow path through the filter assembly stack and filter housing assembly. Advantageously, the first o-ring, the filter membrane, and the membrane backing member are disposed between the bulkhead and cap, with the filter membrane disposed between the first o-ring and the membrane backing member, so that a portion of the cap (e.g., a generally centrally disposed annular shoulder region) presses against part of the membrane backing member so as to compress the first o-ring to create a first seal between the bulkhead and the filter membrane. A second seal advantageously is created by compression of the second o-ring between the bulkhead and cap.

The membrane backing member advantageously comprises a filter frit having a mean path about equal in size to the absolute path of the filter membrane, e.g., advantageously about 0.2 micron. Advantageously, the filter frit comprises a sintered metal filter disk made of titanium, stainless steel, monel, inconel, gold, or another suitable filter material. The frit is disposed downstream of the filter membrane, so as to provide backing support to prevent the filter membrane from bursting under high fluid pressures. A mesh, screen, or other fluid permeable device for providing support, or any combination of one or more of such devices, also may be used instead of or in addition to a filter or a frit as a filter membrane backing member. Advantageously, the filter membrane backing member comprises a relatively smooth member free of sharp edges or rough surfaces that would compromise the filter it backs under pressure.

In an alternate embodiment, the filter assembly stack comprises a filter frame, an o-ring, one or more filter membranes, a membrane backing member, and a filter frame cap. The filter assembly stack advantageously comprises two filter membranes disposed between an o-ring and a membrane backing member. The o-ring, filter membranes, and membrane backing member advantageously are held together between the filter frame and the filter frame cap, with a portion of the filter frame cap pressing against part of the membrane backing member so as to compress the o-ring to form a seal with the filter membrane. The joint between the filter frame and filter frame cap may be sealed with an adhesive, e.g., a UV adhesive. Thus, a sealed fluid pathway through the filter assembly stack is provided. The filter assembly stack is disposed within the filter housing with one or more seals, such as o-rings, disposed between the filter assembly stack and the filter housing bulkhead and cap, to ensure a sealed fluid pathway through the entire assembly. Alternatively, the filter housing bulkhead and cap are adapted with one or more embossed surfaces (raised portions, e.g., formed by one or more ridges or by one or more grooves in the assemblies) that contact the filter frame or filter frame cap upon assembly. Advantageously, the contacting portions of the ridges and/or filter stack are made of deformable materials that compress to form a seal when the filter housing bulkhead and filter housing cap are joined, so that the filter assembly is self-sealing. Alternatively, the filter frame and/or filter frame cap may be adapted to include one or more of such ridges so that the filter assembly is self-sealing, or an o-ring or other such sealing device may be used.

BRIEF DESCRIPTION OF THE DRAWINGS

Further objects and advantages of the present invention will become apparent upon reading the following detailed description and upon referring to the accompanying drawings in which:

FIG. 2 is an exploded, cross-sectional view of an alternate exemplary high pressure fluid filter system in accordance with the present invention.

FIG. 2A is a detail view of a portion of FIG. 2

DETAILED DESCRIPTION OF SPECIFIC EMBODIMENTS

Figure 1:
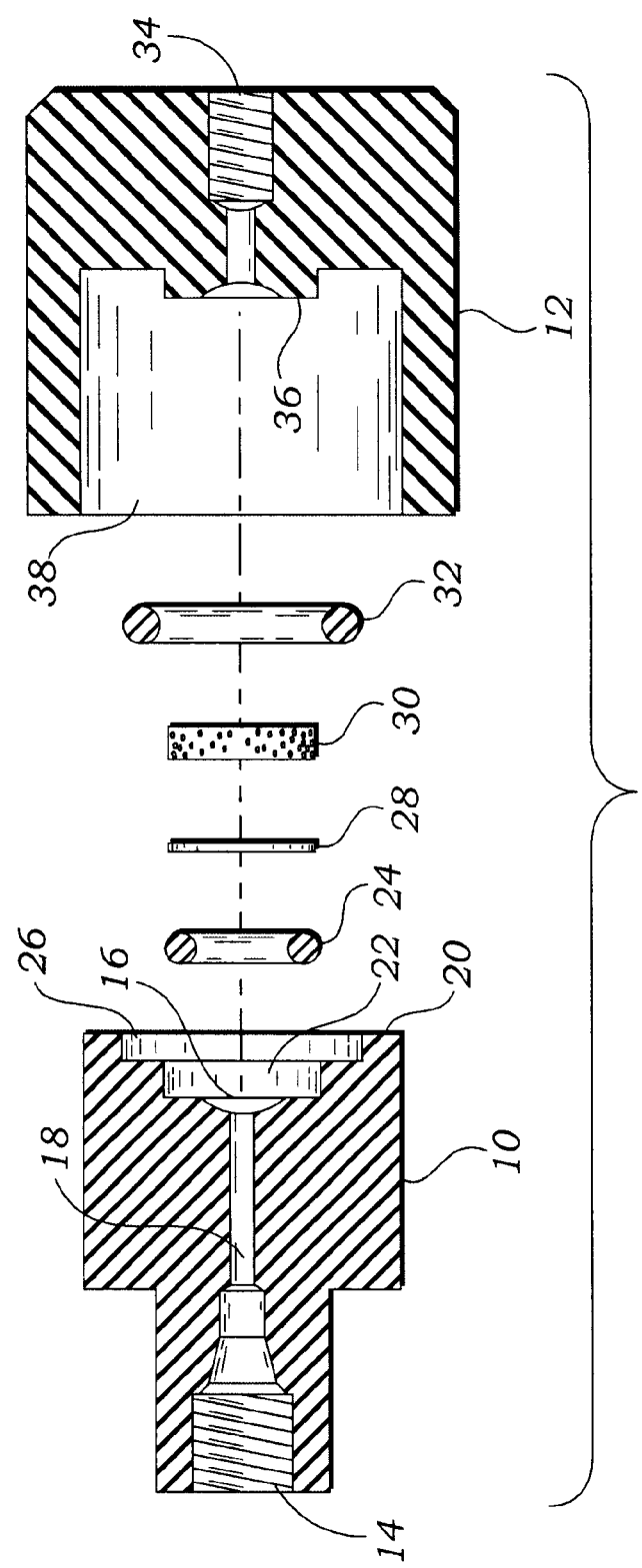
FIG. 1 is an exploded, cross-sectional view of an exemplary high pressure fluid filter system in accordance with the present invention.

The description below illustrates embodiments of the present invention. For the sake of clarity, not all features of an actual implementation of the present invention are described in this specification. It should be appreciated that in connection with developing any actual embodiment of the present invention many application-specific decisions must be made to achieve specific goals, which may vary from one application to another. Further, it should be appreciated that any such development effort might be complex and time-consuming, but would still be routine for those of ordinary skill in the art having the benefit of this disclosure.

For the sake of clarity and convenience, the various embodiments are described herein in the context of applications generally involving the filtering of high pressure fluid streams for medical applications. However, the present invention may also be useful in other, non-medical applications.

Turning now to the drawings, a system is provided for filtering a high pressure fluid stream, i.e., a fluid provided to the filter system at pressures from about 1000 p.s.i. to about 5500 p.s.i. or higher. As shown in FIG. 1, the system includes a filter housing assembly including a bulkhead 10 and cap 12. The exact size and shape of the bulkhead 10 and cap 12 may vary depending upon the circumstances involved in a particular desired application. In the embodiment shown in FIG. 1, the bulkhead 10 comprises a generally cylindrically-shaped block assembly including a continuous fluid pathway comprising a lumen 18 between a fluid inlet 14 and fluid outlet 16. The downstream face 20 of bulkhead 10 advantageously includes a generally cylindrical inner recess 22 within which a first o-ring 24 is positioned to form a seal about the fluid outlet 16. The filter 28 impinges upon the first o-ring 24, so the o-ring 24 provides a first seal between the bulkhead 10 and the filter 28.

The filter 28 advantageously comprises a thin disk of filter media with an absolute path of about 0.5 micron or less, and advantageously of about 0.22 micron or less. For example, a filter media absolute path of about 0.2 micron or less may prove to be particularly advantageous. The filter 28 may be made of nylon, polyethersulfone, teflon, polycarbonate, polyester, polytetrafluoroethylene, polypropylene, cellulose, glass fiber, stainless steel, monel, inconel, silver or gold. Of course, the exact pore size and material selected for use as the filter 28 may vary depending upon the circumstances involved in a particular desired application.

A filter backing member 30 is positioned downstream from the filter 28 to provide backing support to prevent the filter 28 from bursting under high fluid pressures. The filter backing member 30 advantageously comprises a filter frit or disk having a mean path about equal in size to the absolute path of the filter membrane, e.g., advantageously about 0.2 micron or less.

The filter backing member 30 may be a sintered metal filter disk made of titanium, stainless steel, monel, inconel, gold, or another suitable filter material. A mesh, screen, or other fluid permeable device for providing support, or any combination of one or more of such devices, also may be used instead of or in addition to the frit as a filter backing member. The filter backing member 30 advantageously does not compromise the filter 28 under pressure.

The downstream face 20 of bulkhead 10 advantageously includes a generally cylindrical outer recess 26 within which a second o-ring 32 is positioned outside of the filter backing member 30 to form a second seal between the bulkhead 10 and cap 12. The second o-ring 32 advantageously forms the second seal about the continuous fluid pathway between the fluid outlet 16 and the fluid exit lumen 34 through cap 12. It should be mentioned that the o-rings 24 and 32 advantageously are standard-size o-rings made of 70 shore A durometer silicone rubber, although the exact size, shape, hardness, and other properties or characteristics of the o-rings may vary depending upon the particular circumstances involved in a desired application.

The cap 12 advantageously includes a slot or recess 38 adapted to receive the bulkhead 10. The cap 12 and bulkhead 10 may be secured together by threaded engagement, by an adhesive, or by any other suitable joining means. As shown in FIG. 1, the cap 12 also includes a raised shoulder 36 adapted to engage at least a portion of the filter backing member 30 to provide additional support to the filter 28 and the backing member 30. Advantageously, both the first o-ring 24 and the second o-ring 32 are compressed and form seals upon the joining of the cap 12 and bulkhead 10. Thus, a continuous sealed fluid pathway through the filter 28 and filter backing member 30 is provided.

In an alternate embodiment, as shown in FIG. 2, a high pressure fluid bacterial filter assembly is provided comprising a filter assembly stack 40 disposed within a filter housing. Unlike the embodiment of FIG. 1, the filter assembly stack 40 comprises a discrete, disposable filtering unit that may be easily removed from the filter housing and replaced. The filter assembly stack 40 advantageously includes one or more filter membranes 42 disposed between an o-ring 44 and a membrane backing member 46.

Advantageously, the membrane backing member does not compromise the filtering ability of the membranes 42 under pressure. A filter frame 48 including a generally centrally disposed lumen 50 is adapted to receive the o-ring 44, the filter membrane(s) 42, the membrane backing member 46, and a shoulder portion 53 of a filter frame cap 52. The cap 52 also includes a generally centrally disposed lumen 54. Advantageously, upon the joining of the filter frame 48 and filter frame cap 52, the o-ring 44 is compressed so as to create a sealed fluid pathway through the filter assembly stack 40. The filter frame 48 and the filter cap 52 are advantageously sealed together, with an adhesive, for instance, such as a UV adhesive. Also, to ensure that the stack 40 is properly positioned for fluid flow, the frame 48 and/or the cap 52 may include a key or key way (not shown) that corresponds to a complementary key way or key (not shown) in the bulkhead 56 and/or the plug 58.

The filter assembly stack 40 advantageously is disposed within the filter housing which comprises a bulkhead 56 and a plug or nut 58. The bulkhead 56 includes a generally centrally disposed lumen 60 adapted to receive a supply of high pressure fluid. Also, one or more ridges 62 are disposed about the lumen 60 and positioned to contact the filter frame 48. Advantageously, the ridges 62 and/or the filter frame 48 are made of a deformable material, such as polyethersulfone, polycarbonate, polyester or other suitable material, so that when the nut 58 is joined with the bulkhead 56 the filter frame 48 is forced against the ridges 62 to form one or more seals about the continuous fluid pathway running through lumens 50,60. The nut 58 includes a generally centrally disposed fluid exit lumen 64, and also may include one or more ridges 62 (see FIG. 2A) positioned to contact the filter cap 52. Thus, upon the joining of the bulkhead 56 and the nut 58, a continuous sealed fluid pathway is provided through the filter assembly stack and the filter housing. Of course, another suitable seal, such as an O-ring, may be used along with or instead of the ridges 62.

The present invention may be susceptible to various modifications and alternative forms. Specific embodiments of the present invention are shown by way of example in the drawings and have been described herein in detail. It should be understood, however, that the description set forth herein of specific embodiments is not intended to limit the present invention to the particular forms disclosed. Rather, all modifications, alternatives, and equivalents falling within the spirit and scope of the invention as defined by the appended claims are intended to be covered.

What is claimed is:

1. A bacterial fluid filtration device comprising:
    a filter housing having an axial fluid passageway extending therethrough and having a removable filter assembly disposed therein, wherein the filter housing comprises:
        a bulkhead portion having a first fluid inlet;
        a first seal disposed about the first fluid inlet; and
        a plug portion having a first fluid outlet, the plug portion being coupleable to the bulkhead portion;
    and wherein the removable filter assembly comprises:
        a filter frame having a second fluid inlet and a second fluid outlet;
        a second seal disposed about the second fluid inlet of the filter frame;
        at least one filter element disposed adjacent the second seal, the at least one filter element having an absolute path; and
        a backing element disposed adjacent the at least one filter element to support the at least one filter element at pressures of at least about 1000 psi, the backing element having a mean path substantially equal to the absolute path of the at least one filter element.

2. The fluid filtration device, as set forth in claim 1, wherein the filter element comprises a disk.

3. The fluid filtration device, as set forth in claim 1, wherein the filter element comprises at least one of nylon, polyethersulfone, teflon, polycarbonate, polyester, polytetrafluoroethylene, polypropylene, cellulose, glass fiber, stainless steel, monel, inconel, silver or gold.

4. The fluid filtration device, as set forth in claim wherein the filter element comprises an absolute path of about 0.22 micron or less.

5. The fluid filtration device, as set forth in claim 1, wherein the backing element comprises a disk.

6. The fluid filtration device, as set forth in claim 1, wherein the backing element comprises at least one of sintered metal filter disk made of at least one of titanium, stainless steel, monel, inconel, and gold.

7. The fluid filtration device, as set forth in claim 1, wherein the backing element comprises an absolute path of about 0.5 micron or less.

8. The fluid filtration device, as set forth in claim 1, wherein the first seal disposed about the first fluid inlet of the bulkhead portion comprises a deformable ring formed integral with the bulkhead portion.

9. The fluid filtration device, as set forth in claim 1, wherein the first seal disposed about the first fluid inlet of the bulkhead portion comprises an o-ring seal.

10. The fluid filtration device, as set forth in claim 1, wherein the bulkhead portion and the plug portion of the filter housing are threadably engageable.

11. The fluid filtration device, as set forth in claim 1, wherein the second seal comprises o-ring.

12. The fluid filtration device, as set forth in claim 1, wherein the filter assembly further comprises a cap having a second fluid outlet wherein the cap is coupleable to the filter frame.

* * * * *